United States Patent [19]

Pardridge

[11] Patent Number: 4,992,255
[45] Date of Patent: Feb. 12, 1991

[54] CAPILLARY DEPLETION METHOD FOR QUANTIFYING TRANSCYTOSIS THROUGH THE BLOOD-BRAIN BARRIER

[76] Inventor: William M. Pardridge, 1180 Tellem Dr., Pacific Palisades, Calif. 90272

[21] Appl. No.: 286,244

[22] Filed: Dec. 19, 1988

[51] Int. Cl.$^5$ .......................... G01N 37/00; A61B 6/00
[52] U.S. Cl. ........................................ 424/1.1; 436/56; 128/654; 250/303
[58] Field of Search ........................... 424/1.1; 534/14; 128/654; 600/3; 436/56, 804; 250/303

[56] References Cited

U.S. PATENT DOCUMENTS

| | | | |
|---|---|---|---|
| 4,392,996 | 7/1983 | Sternberger | 424/95 X |
| 4,638,051 | 1/1987 | Burns et al. | 424/1.1 X |
| 4,707,544 | 11/1987 | Jones et al. | 424/1.1 X |
| 4,716,905 | 1/1988 | Schmued | 128/654 |
| 4,765,972 | 8/1988 | Safa et al. | 424/1.1 |

OTHER PUBLICATIONS

B. V. Zlokovic, D. J. Begley, B. M. Djuricic, and D. M. Mitrovic, "Measurement of Solute Transport Across the Blood-Brain Barrier in the Perfused Guinea Pig Brain: Method and Application to N-Methyl Aminoisobutyric Acid", Journal of Neurochemistry, New York, 1986 International Society for Neurochemistry, pp. 1444–1451.
Y. Takasato, S. I. Rapoport, and Q, R. Smith, "An in Situ Brain Perfusion Technique to Study Cerebrovascular Transport in the Rat", Laboratory of Neurosciences, National Institute on Aging, National Institutes of Health, Bethesda, Md., 20205, Am. J. Physiol. 247 (Heart Circ. Physiol. 16):H484–H493, 1984.
W. M. Pardridge, J. Eisenberg, and T. Yamada, "Rapid Sequestration and Degradation of Somatostatin Analogues by Isolated Brain Microvessels", Journal of Neurochemistry, Raven Press, N.Y., 1985 International Society for Neurochemistry, pp. 1178–1184.
W. M. Pardridge, J. Eisenberg, and W. T. Cefalu, "Absence of Albumin Receptor on Brain Capillaries in Vivo or in Vitro", Am. J. Physiol. 249 (Endocrinol. Metab. 12):E264–E267, 1985.

Primary Examiner—John S. Maples

[57] ABSTRACT

A method for quantifying transcytosis through the blood-brain barrier by infusing a perfusate into the brain of a living mammal. The perfusate includes a radio-labelled test compound and a radio-labelled marker compound. The perfused brain is removed from the animal and homogenized. The homogenized brain is separated into a microvasculature fraction and a supernatant fraction. The net volume of distribution of the test compound in the supernatant is calculated and corrected to provide an accurate measure of transcytosis through the blood brain barrier.

9 Claims, 1 Drawing Sheet

CAPILLARY DEPLETION METHOD FOR QUANTIFYING TRANSCYTOSIS THROUGH THE BLOOD-BRAIN BARRIER

This invention was made with Government support under Contract No. DAMD17-87-C-7137 awarded by the Department of Defense (Army). The Government has certain rights in this invention.

BACKGROUND OF THE INVENTION

1. Field of the Invention

The present invention involves the blood-brain barrier and methods for determining the degree of transcytosis of peptides or plasma proteins across the blood-brain barrier.

2. Description of Related Art

The vertebrate brain has a unique capillary system which is unlike that in any other organ in the body. The unique capillary system has morphologic characteristics which make up the blood-brain barrier (BBB). The blood-brain barrier acts as a systemwide cellular membrane which separates the brain interstitial space from the blood.

The unique morphologic characteristics of the brain capillaries which make up the BBB are: (a) epitheliallike high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry are very low.

Various strategies have been developed for introducing such hydrophilic drugs and peptides into the brain, which otherwise would not cross the blood-brain barrier. The most widely used strategies involve invasive procedures where the drug is delivered directly into the brain. The most common procedure is the implantation of a catheter into the ventricular system to bypass the blood-brain barrier and deliver the drug directly to the brain.

Recently, techniques have been discovered for altering hydrophilic drugs and peptides so that they can be delivered to the brain by receptor-mediated transcytosis through the blood-brain barrier. For example, chimeric peptides have been prepared which include a peptide, which by itself, is capable of crossing the blood-brain barrier by transcytosis at a relatively high rate. This transportable peptide is conjugated to a hydrophilic neuropeptide which, by itself, is transportable only at a very low rate into the brain across the blood-brain barrier. The resulting chimeric peptide is transported into the brain at a much higher rater than the neuropeptide alone. Details of such chimeric peptides are set forth in U.S. patent application Ser. No. 06/892,067, filed on July 30, 1986.

Other techniques for increasing transcytosis of hydrophilic drugs and peptides across the blood-brain barrier include cationization of antibodies used in treatment and diagnosis of neurological diseases. It has been found that cationization of antibodies renders them transportable through the blood-brain barrier by transcytosis. Details of cationized antibodies for delivery through the blood-brain barrier are set forth in U.S. patent application Ser. No. 07/085,627, filed on Aug. 17, 1987.

In view of the development of substances that are capable of crossing the blood-brain barrier by transcytosis, there is presently a need to provide a routine and quantitative methodology for rapidly accessing the degree of transport by transcytosis through the cellular endothelial barrier in the brain capillaries. Presently, morphologic methods are available, such as autoradiography or immunocytochemistry. Both of these methods involve exposing the brain to various compounds followed by sectioning of the brain and measurement of the compound distribution.

The autoradiographic method, although sensitive, is very slow. This method requires several months, delay for adequate exposure of the emulsions so that proper assessment of radio-activity in the brain tissue can be made. Immunocytochemistry is more rapid than the autoradiographic method. However, the immunocytochemistry method is very insensitive and therefore, is unsuitable for use in detecting minute amounts of material which may be transported across the blood-brain barrier.

As is apparent, there is a need to provide a simple, efficient and quantitative method for measuring the transcytosis of compounds through the blood-brain barrier so that an accurate assessment can be made regarding the compound's usefulness in the diagnosis or treatment of neurological diseases.

SUMMARY OF THE INVENTION

In accordance with the present invention, a method is disclosed which is relatively simple, quick and provides a quantitative measurement of the transcytosis of a peptide or protein through the blood-brain barrier.

The present invention is based upon a method wherein a perfusate solution is perfused through the brain of a living mammal while the brain is still in the mammal. The perfusate solution includes a test compound for which transcytosis across the blood-brain barrier is to be measured. The test compound is labelled with a first radio-active label. Also included in the perfusate solution is a marker compound which is labelled with a second radio-active label. The marker compound is not capable of passing through the blood-brain barrier of the mammal and further, must be of approximately the same size as the test compound.

After perfusion, at least a portion of the brain is removed from the mammal and homogenized to form a brain homogenate. The homogenate is separated into a brain vascular tissue fraction and a supernatant fraction. The radio-activity of the first and second radio-active labels in the perfusate and the supernatant is measured. Using these two measurements, the volume of distribution of the first and second radio-active labels in the supernatant is calculated. The quantitative determination of transcytosis of the test compound across the blood-brain barrier is then determined by subtracting the volume of distribution of the second radio-active label present on the marker compound from the volume of distribution of the first radio-active label on the test compound.

The above method provides an accurate and quantitative measurement of transcytosis across the blood-brain barrier as opposed to binding/adsorption and endocytosis by brain vasculature.

The above discussed and many other features and attendant advantages of the present invention will become better understood by reference to the following detailed description when considered in conjunction with the accompanying drawings.

DETAILED DESCRIPTION OF THE INVENTION

Figure 1:
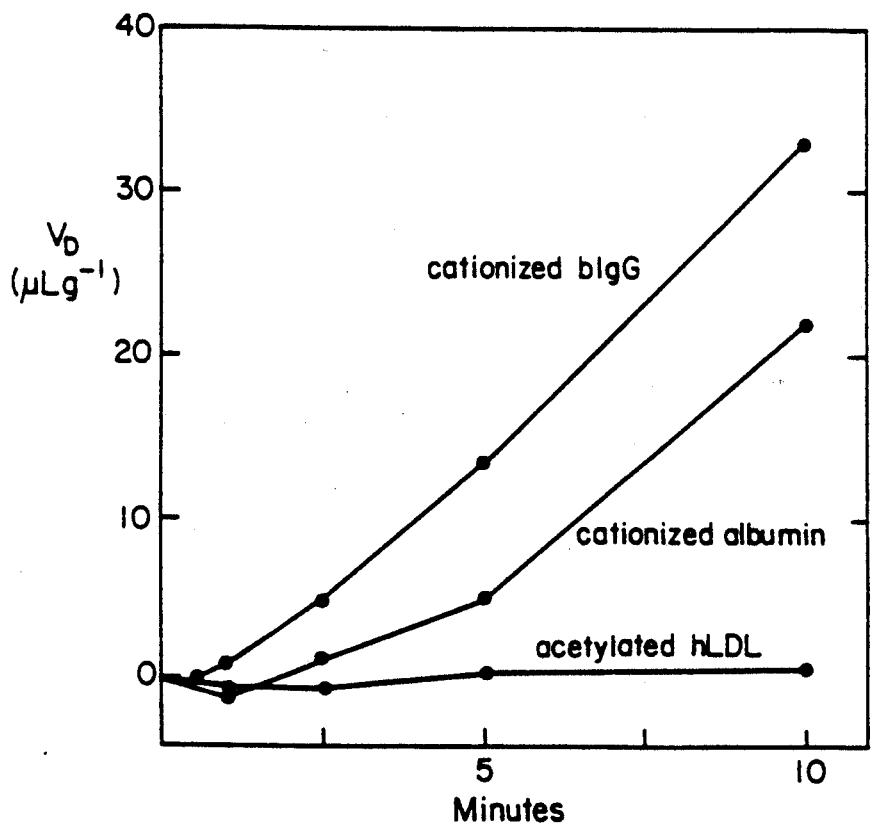
FIG. 1 is the corrected or net volume distribution of cationized albumin, cationized immunoglobulin and acetylated low-density lipoprotein in the supernatant fraction separated from the brain homogenate.

The present invention is designed to quantitatively measure transcytosis of compounds across the blood-brain barrier. In this context, transcytosis means the movement of the compound away from the antilumenal membrane of the brain capillary and into the brain parenchyma. This is to be distinguished from mere binding, adsorption or endocytosis of the compound into the brain capillary endothelial cytoplasm.

The typical compounds for which measurements of transcytosis are desired include peptides and proteins used in treating and diagnosing neurological functions. Such compounds include the chimeric peptides and cationized antibodies referred to in the previously mention U.S. patent applications. However, the method is not limited to these types of compounds and may be used to determine transcytosis across the blood-brain barrier of a wide variety of compounds. Preferably, the compound of interest (i.e., the test compound) will be a protein or peptide which is believed to have some value for treating or diagnosing neurological function.

The initial step in the process involves preparing a perfusate solution which includes a test compound and a marker compound. The perfusate solution may be any of the plasma or synthetic perfusate solutions commonly used in perfusing mammal brains. The perfusate preferably will include up to 25% red blood cells. Since the perfusion process is carrier out on a living mammal, the use of red blood cells is preferred in the perfusate solution since it allows the increase of perfusion time, if desired.

The test compound is labelled with a first radioactive label. Any suitable radio-active label can be used with $^{125}I$ being preferred. The marker compound is labelled with a second radio-active label, which must be different from the radio-active label used to label the test compound. Preferably, the second radio-active label is $^3H$. Of course, other radio labels may be used.

The marker compound must be a compound which is not capable of transcytosis across the blood-brain barrier. As a result, the marker compound provides a measurement of capillary leakage. As will be discussed in more detail below, the leakage of test compound from the capillaries during the homogenization step must be corrected for in order to provide an accurate quantitative measurement of transcytosis. The use of a radio labelled marker compound provides a method for making this correction. In this regard, it is necessary that the marker compound have a molecular weight which is approximately the same as the test compound. It is preferred that the molecular weight of the marker compound be within ten percent (10%) of the molecular weight of the test compound. However, acceptable results may be obtained with marker compounds having molecular weights that vary from the test compound molecular weight by no more than sixty percent (60%). Preferred marker compounds include albumin and inulin which have been radio labelled with $^3H$.

The amounts of test compound and marker compound present in the perfusate solution should be within the range of 1 to 25 micro Ci/ml. The concentration of test compound is preferably around 1 to 10,000 mg/ml., with the concentration of marker compound preferably being about 1 to 10,000 mg/ml.

The perfusate solution is perfused into the brain of a living mammal while the brain is still in the mammal. Perfusion is accomplished through the carotid artery in accordance with known in situ brain perfusion techniques, such as those disclosed by Yoshio Takasato, et al., An In Situ Brain Perfusion Technique To Study Cerebral Transport In Rat, "American Journal of Physiology", Vol. 247, "Heart Circulation Physiology" 16:H484–H493, 1984 or in Berislav V. Zlokovic, Measurement Of Solute Transport Across The Blood-Brain Barrier In Perfused Guinea Pig Brain, "Journal of Neurochemistry", pp. 1444–1451, 1986. Both of these articles, along with other articles and patents or patent applications mentioned in the specification are hereby incorporated by reference. The procedure for in situ brain perfusion is well known and will not be discussed in detail.

With solutions that do not contain red blood cells, the perfusate solution is perfused through the brain for a period of up to ten minutes. For solutions that do contain red blood cells, the time of perfusion may be extended up to thirty minutes.

After the perfusion is completed, the mammal is sacrificed and the brain is removed and weighed and is then homogenized in accordance with brain homogenization procedures. The resulting homogenate is then placed in a density gradient medium for separation by centrifugation into a solid pellet containing brain vascular tissue and a supernatant fraction. Any suitable density gradient medium can be used to accomplish the separation. Density gradient materials such as dextran, Percoll ® and sucrose may be used. A thirteen percent (13%) by weight/volume aqueous solution of dextran is preferred. The centrifugal force applied during the separation, as well as the actual centrifugation time may be varied so long as a suitable separation of the supernatant fraction from the brain vascular tissue fraction is accomplished.

The procedure for separation of the homogenate into supernatant and solid fractions is described in detail in Pardridge, et al., Rapid Sequestration and Degradation of Somatostatin Analogues by Isolated Brian Microvessels, "Journal of Neurochemistry", 44, 1178–1184 (1985).

After separation, the supernatant fraction is measured to determine the radio-activity of both the first and second radio-active labels present on the test compound and marker compound, respectively. In addition, the radio-activity of both the first and second radio-active labels in the perfusate solution is determined prior to the perfusion step. The volume distribution of the compounds in the supernatant is then calculated according to the following equations:

$$V_{D1} = \frac{dpm1 \text{ in total supernatant/g. of brain}}{dpm1/\text{microliter perfusate}}$$

-continued $$V_{D2} = \frac{dpm2 \text{ in total supernatant/g. of brain}}{dpm2/\text{microliter perfusate}}$$

where
$V_{D1}$ = volume of distribution of test compound in the supernatant.
$V_{D2}$ = volume of distribution of the marker compound in the supernatant.
dpm1 = disintegrations per minute of first radio-active label on the test compound.
dpm2 = disintegrations per minute of second radio-active label on the marker compound.

The net volume distribution of the test compound in the supernatant, which is due to transcytosis only, is then calculated by substrating $V_{D2}$ from $V_{D1}$. The subtraction of the marker volume of distribution from the test compound volume of distribution in the supernatant provides a correction factor for leakage from the brain capillaries during homogenization. This correction removes any possibility of capillary leakage being misinterpreted as transcytosis. The use of $^3$H-albumin as a marker compound of brain vascular space is disclosed in William Pardridge, et al., Absence of Albumin Receptor on Brain Capillaries In Vivo or In Vitro, "American Journal of Physiology", 249 (Endocrine Metabolism 12): E264–E267 (1985).

The procedure, as set forth above, provides a quantitative measure of transcytosis only across the brain barrier. Any portion of the test compound which may have undergone endocytosis by the vasculature (but not transcytosis) or may have otherwise been bound to the brain capillary tissue is separated out during the process to prevent possible interference with the transcytosis measurement.

Examples of practice are as follows:

EXAMPLE 1

A laboratory rat was anesthetized using intramuscular injection of ketamine/xylazine. An external carotid artery was exposed and cannulated with PE-10 tubing. A ligature was loosely placed around the common carotid artery. The minor arteries, such as the ophthalmic artery or the thyroidal artery, that emanate from the carotid artery were cauterized. The pterygopalatine artery was similarly cauterized.

The PE-10 tubing was connected to a reservoir containing a physiologic-balanced salt solution, which contained radio-labelled human low density lipoprotein (hLDL) and radio-labelled albumin. The LDL was radio-labelled with $^{125}$I according to the iodine monochloride procedure of Shepherd, et al., Radioiodination of Human Low Density Lipoprotein: A Comparison of Four Methods, "Clinica Chimica Acta", 66 (1976) 97–109. The albumin was radio-labelled or marked with $^3$H according to the procedure of William Pardridge, et al., Absence of Albumin Receptor on Brain Capillaries In Vivo or In Vitro, "American Journal of Physiology", 249 (Endocrine Metabolism 12): E264–E267 (1985). The perfusate solution further included three percent (3%) by weight albumin to maintain oncotic pressure and no rat red blood cells, since perfusions were limited to 10 minutes.

At the initiation of the perfusion, the perfusate solution was infused at a rate of 1 ml per minute with a peristaltic or syringe pump and the common carotid artery was ligated. The perfusate solution was infused at various times from 1–10 minutes. To maintain normal blood volume, a catheter was placed into a peripheral vein and blood was removed at a rate of one milliliter per minute. The removal rate of blood from the peripheral vein was the same rate as the carotid artery infusion.

At various times after injection, such as 1, 2.5, 5 or 10 minutes, the animal was decapitated and the brain homogenized in 5 ml of balanced salt solution containing 13% Dextran (molecular weight approximately 60,000–80,000).

The homogenate in dextran solution was then centrifuged at 5,500 G for 15 minutes at 4° C. The total volume of supernatant was measured and the supernatant was then decanted in a 1 ml aliquot and counted simultaneously for [$^{125}$I]and [$^3$H]radio-activity. Similarly, the pellet, which comprised the brain microvasculature was also counted for [$^{125}$I]and [$^3$H]. In addition, prior to centrifugation, a sample of the homogenate was removed and counted for [$^{125}$I]and [$^3$H]. The radioactivities for the supernatant, brain microvasculature and homogenate were recorded in DPMs. In addition, prior to each perfusion, the radio-activity of the perfusate solution was also measured for [$^{125}$I]and [$^3$H]. The $V_{D1}$ and $V_{D2}$ for the supernate was determined in accordance with the previously described equations and the net volume distribution or transcytosis calculated. The results of the method carried out over perfusion times of 1, 2.5, 5 and 10 minutes are set forth in FIG. 1. As can be seen, the net volume distribution of hLDL in the perfusate is zero. This is consistent with the known fact that hLDL is not transcytosed across the blood-brain barrier.

Figure 2:
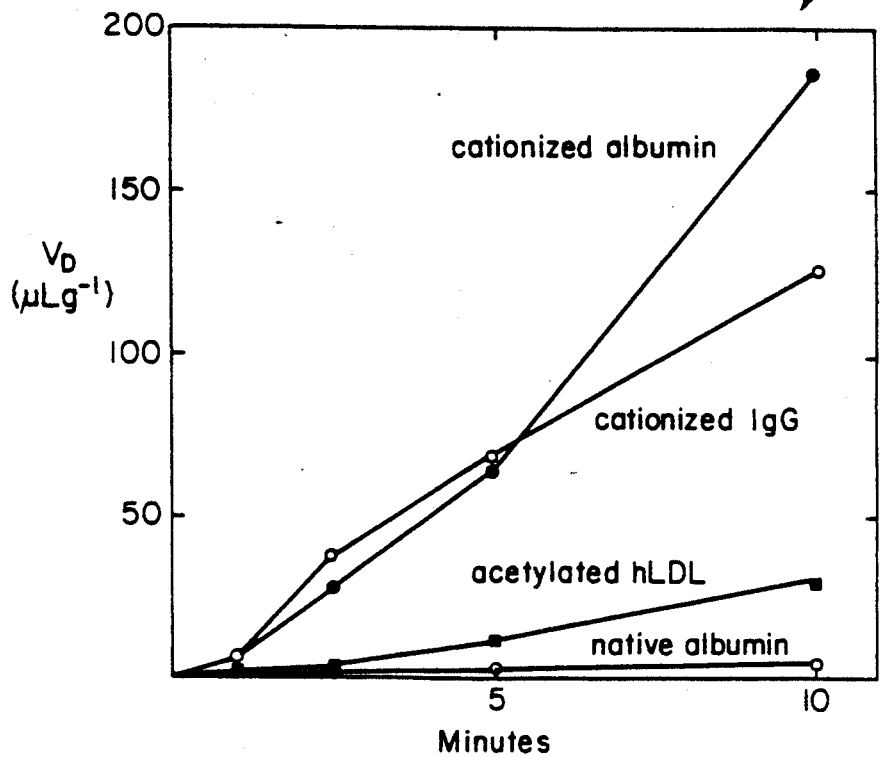
FIG. 2 is a graphic representation of the uncorrected or net volume of distribution of cationized albumin, cationized immunoglobulin and acetylated low-density lipoprotein in a total brain homogenate.

The volume distribution of hLDL within the brain was also calculated utilizing the radio-activity values measured for the homogenate. The results are shown in FIG. 2. As can be seen, the volume distribution of hLDL in the brain reaches approximately 30 microliter per gram of brain. This measurement, however, includes hLDL which is endocytosed and otherwise bound to the brain vasculature. Accordingly, it is not suitable for determining transcytosis. Determination of the volume distribution in the homogenate is, however, of value in providing general information on binding of the hLDL to the brain vasculature. In addition, if desired, further quantitative information regarding overall binding of the hLDL to the tissue can be obtained by calculating volume distribution based on the radio-activity measured for the microvasculature pellet.

EXAMPLE 2

The perfusion process set forth in Example 1 was also carried out using cationized albumin as the test compound instead of hLDL. The cationized albumin was obtained by Kumagai, et al., Absorptive-mediated Endocytosis of Cationized Albumin and a Beta-Endorphin-cationized Albumin Chimeric Peptide by Isolated Brain Capillaries, "The Journal of Biological Chemistry", Vol. 262, No. 31, Issue of Nov. 5, pp. 15215–15219, 1987. The marker compound utilized in this example also was [$^3$H]albumin.

The results of this Example are also set forth in FIGS. 1 and 2. The calculations of volume distribution in the supernatant and homogenate were calculated in the same manner as Example 1. As can be seen in FIG. 1, the cationized albumin was transcytosed across the blood-brain barrier. This correlates to the known ability of cationized albumin to be endocytosed across the BBB. Again, the results depicted in FIG. 2 shows that cationized albumin is rapidly taken up by the brain, not only through transcytosis, but endothelial uptake. Accordingly, measurement of the volume distribution in the homogenate does not provide a true measure of transcytosis. A true measure of transcytosis is only provided in accordance with the present invention wherein volume distribution of the supernatant is measured

EXAMPLE 3

The perfusion procedure set forth in Example 1 was again carried out, except that cationized immunoglobulin was substituted for hLDL. The cationized immunoglobulin was obtained by cationizing immunoglobulin according to methods described for cationization of albumin, Kumagai, et al., Absorptive-mediated Endocytosis of Cationized Albumin and a Beta-Endorphin-cationized Albumin Chimeric Peptide by Isolated Brain Capillaries, "The Journal of Biological Chemistry", Vol. 262, No. 31, Issue of Nov. 5, pp. 15215–15219, 1987. The marker compound was $^3$H-albumin. Radio labelling was carried out in accordance with Example 1.

Radio-activities were measured and the various volume distributions were calculated as in Example 1. The results of this perfusion study are also shown in FIGS. 1 and 2.

FIG. 1 shows that cationized immunoglobulin is transcytosed into the brain at a higher rater than cationized albumin. This is to be contrasted with FIG. 2 which shows that cationized albumin has a higher overall uptake by the brain after ten minutes. As is clear, the endothelial uptake of a compound is not necessarily directly related to transcytosis across the blood-brain barrier. Accordingly, measurements of the compound uptake in the brain homogenate can be misleading as a measure of transcytosis. However, the present method, which measures volume distribution in the supernatant only, provides an accurate quantitative measurement of transcytosis.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A method for measuring the transcytosis of a compound through the blood-brain barrier, said method comprising the steps of:

(a) perfusing a perfusate solution through the brain of a living mammal while said brain is in said mammal, said perfusate solution including:
test compound for which transcytosis across said blood-brain barrier is to be measured, said test compound being labelled with a first radio-active label; and
a marker compound which is labelled with a second radio-active label, wherein said marker compound is not capable of passing through the blood-brain barrier of said mammal and wherein said marker compound is approximately the same size as said test compound;

(b) removing at least a portion of the brain said mammal and weighing this brain;

(c) homogenizing a portion of the brain removed from said mammal to form a brain homogenate;

(d) separating said brain homogenate into a brain vascular tissue fraction and a supernatant fraction;

(e) determining the radio-activity of said first and second radio-active labels in said perfusate solution;

(f) measuring the radio-activity level of said first and second radio-active labels in said supernatant fraction;

(g) computing the volume distribution of said first and second radio-active labels in said supernatant;

(h) determining the transcytosis of said test compound across said blood-brain barrier by subtracting the volume of distribution of said second radio-active label from the volume of distribution of said first radio-active label.

2. A method according to claim 1 wherein said second radio-active label is $^3$H.

3. A method according to claim 1 wherein said perfusate solution includes blood cells.

4. A method according to claim 1 wherein said test compound is a peptide or a protein.

5. A method according to claim 4 wherein said protein comprises cationized albumin or cationized immunoglobulin.

6. A method according to claim 1 wherein said first radio-active label is $^{125}$I.

7. A method according to claim 6 wherein said second radio-active label is $^3$H.

8. A method according to claim 1 wherein the step of separating said brain homogenate into a brain vascular tissue fraction and a supernatant fraction comprises the step of centrifuging said homogenate in a density gradient media.

9. A method according to claim 8 wherein said density gradient media comprises approximately 13 percent dextran (weight to volume).

* * * * *